United States Patent
Yamaguchi et al.

[11] Patent Number: 6,060,618
[45] Date of Patent: May 9, 2000

[54] FLUORINE-CONTAINING AMIDE COMPOUND

[75] Inventors: Kouichi Yamaguchi; Yasushi Yamamoto; Masatoshi Arai, all of Gunma-ken, Japan

[73] Assignee: Shin Etsu Chemical Co., Ltd., Tokyo, Japan

[21] Appl. No.: 09/356,027

[22] Filed: Jul. 16, 1999

[30] Foreign Application Priority Data

Jul. 16, 1998 [JP] Japan ................................. 10-202143

[51] Int. Cl.⁷ ..................................................... C07F 7/10
[52] U.S. Cl. ............................................................. 556/419
[58] Field of Search ............................................. 556/419

[56] References Cited

U.S. PATENT DOCUMENTS

| | | | |
|---|---|---|---|
| 5,554,779 | 9/1996 | Sato et al. | 556/419 |
| 5,665,846 | 9/1997 | Sato et al. | 528/15 |
| 5,705,586 | 1/1998 | Sato et al. | 528/15 |
| 5,936,111 | 8/1999 | Tarumi et al. | 556/419 |

*Primary Examiner*—Paul F. Shaver
*Attorney, Agent, or Firm*—Millen, White, Zelano & Branigan, P.C.

[57] ABSTRACT

Disclosed is a novel compound which is a perfluoroalkylene dianilide compound represented by the general formula

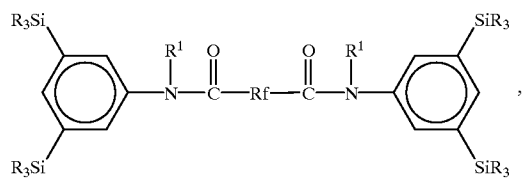

in which Rf is a perfluoroalkylene group optionally interruptrd by oxygen atoms to form an ether linkage and R and $R^1$ are each a hydrogen atom or a monovalent hydrocarbon group. When this compound has two or more hydrogen atoms directly bonded to the silicon atoms in a molecule, the compound is useful as a crosslinking agent for an organosilicon compound having two or more silicon-bonded vinyl groups in a molecule. Alternatively, the compound having two or more silicon-bonded vinyl groups in a molecule is useful as a crosslinking agent for an organosilicon compound having two or more silicon-bonded hydrogen atoms in a molecule. The dianilide compound is prepared by the coupling reaction between a perfluoroalkylene dicarboxylic acid difluoride and an N-trimethylsilyl-N-(3,5-disilylphenyl) amine compound.

16 Claims, 1 Drawing Sheet

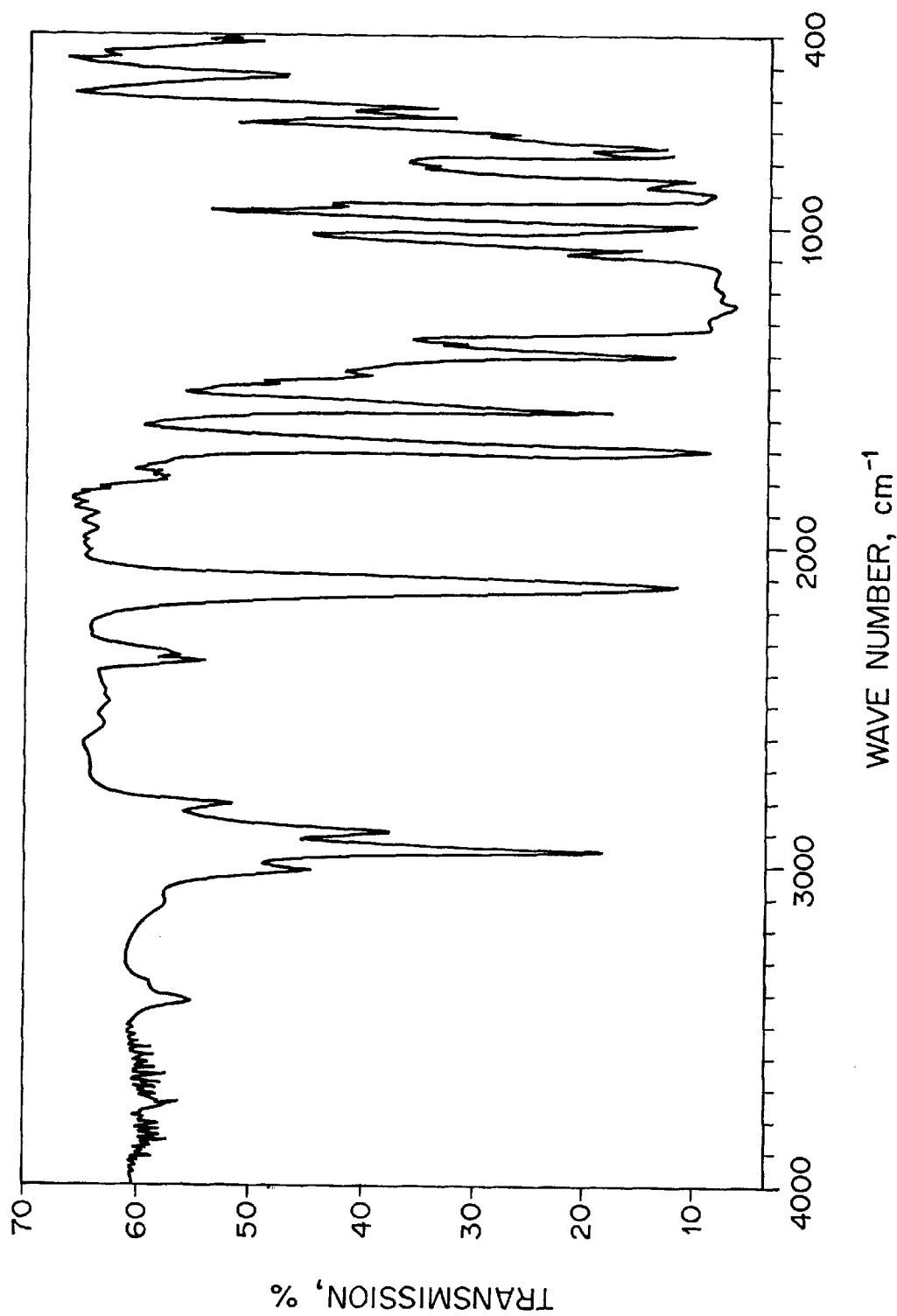
FIGURE

FLUORINE-CONTAINING AMIDE COMPOUND

BACKGROUND OF THE INVENTION

The present invention relates to a novel amide compound containing fluorine atoms not described in any prior art literature or, more particularly, to a fluorine-containing aromatic diamide compound substituted on each of the benzene rings by two organosilyl groups, which may be useful as a crosslinking agent of a curable silicone rubber composition. The invention further relates to a method for the preparation of the above mentioned novel compound.

While several types are known of silicone rubber compositions curable by utilizing a crosslinking agent and various compounds are proposed and employed as the crosslinking agent for silicone rubber compositions, none of the conventional crosslinking agents are quite satisfactory with problems related to the insufficient activity for curing of the silicone rubber composition and expensiveness of the compound. Accordingly, the inventors have conducted extensive investigations to obtain a compound useful as a crosslinking agent of silicone rubber compositions free from the above mentioned problems and disadvantages in the conventional crosslinking agents including screening tests of known compounds and synthetic preparation of novel compounds to be subjected to a curing test of silicone rubber compositions. As a result of these studies, the inventors have arrived at an unexpected discovery that a novel fluorine-containing diamide compound specified below is quite satisfactory for the purpose.

SUMMARY OF THE INVENTION

Thus the novel fluorine-containing diamide compound unexpectedly discovered as a result of the above mentioned synthetic studies is a perfluoroalkylene dianilide compound represented by the general formula

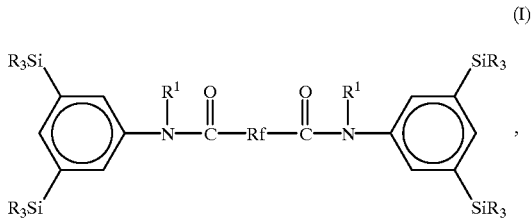

(I)

in which each R is, independently from the others, a hydrogen atom or a monovalent hydrocarbon group, each $R^1$ is, independently from the other, a hydrogen atom or a monovalent hydrocarbon group and Rf is a perfluoroalkylene group having 1 to 14 carbon atoms or a perfluoroalkylene group having at least 2 carbon atoms and interrupted by at least one oxygen atom between adjacent carbon atoms to form an ether linkage, referred to as a perfluoropolyether group hereinafter.

The synthetic method for the preparation of this novel compound will be clear from the description given later.

BRIEF DESCRIPTION OF THE DRAWING

The FIGURE of the accompanying drawing is an infrared absorption spectrum of the inventive compound prepared in the Example.

DETAILED DESCRIPTION OF THE PREFERRED EMBODIMENTS

As is defined above in terms of the general formula (I), the inventive fluorine-containing amide compound is a perfluoroalkylene dianilide compound substituted with silyl groups at the 3- and 5-positions on each of the phenyl groups. In the general formula (I), Rf is a perfluoroalkylene group which is a divalent group expressed by the formula $-C_nF_{2n}-$, in which the subscript n is a positive integer not exceeding 14 or, preferably, in the range from 4 to 8. The carbon atom chain in this perfluoroalkylene group can optionally be interrupted by one or more of oxygen atoms forming an ether linkage or linkages between adjacent carbon atoms in the alkylene chain. Such a perfluoroalkylene group having an ether linkage is referred to as a perfluoropolyether group.

Examples of the perfluoropolyether groups as a class of Rf include those expressed by the following general formulas:

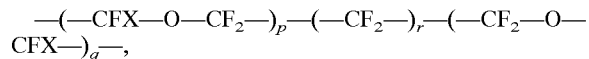

in which X is a fluorine atom or a trifluoromethyl group, the subscripts p and q are each, independently from the other, a positive integer with the proviso that p+q does not exceed 200 or, preferably, 100 and the subscript r is 0 or a positive integer not exceeding 6;

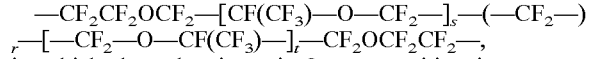

in which the subscript r is 0 or a positive integer not exceeding 6 and the subscripts s and t are each, independently from the other, 0 or a positive integer with the proviso that s+t is a positive integer not exceeding 200 or, preferably, in the range from 2 to 100;

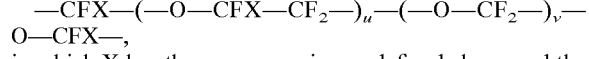

in which X has the same meaning as defined above and the subscripts u and v are each, independently from the other, a positive integer not exceeding 100; and

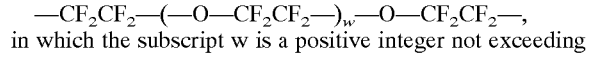

in which the subscript w is a positive integer not exceeding 100.

Particular examples of the divalent groups denoted by Rf in the general formula (I) include those expressed by the following formulas: $-C_4F_8-$; $-C_6F_{12}-$; $-[CF(CF_3)-O-CF_2-]_n-[-CF_2-O-CF(CF_3)-]_m-$, n+m being an integer in the range from 2 to 200; $-CF_2CF_2OCF_2CF(CF_3)-(-CF_2)_4-OCF(CF_3)\ CF_2OCF_2CF_2-$; $-CF(CF_3)-[-OCF(CF_3)-CF_2-]_n-(-OCF_2-)_m-OCF(CF_3)-$, n being an integer of 5 to 100 and m being a positive integer not exceeding 100; $-CF_2CF_2O-(-CF_2-)_4-OCF_2CF_2-$; $-CF_2-(-OCF_2CF_2-)_n-(-OCF_2-)_m-OCF_2-$, n being an integer of 5 to 100 and m being a positive integer not exceeding 100; and $-CF_2CF_2-(-OCF_2CF_2CF_2-)_n-OCF_2CF_2-$, n being an integer of 5 to 100.

The group denoted by $R^1$ in the general formula (I) bonded to each of the amide-nitrogen atoms is a hydrogen atom or a monovalent hydrocarbon group exemplified by alkyl groups such as methyl, ethyl and propyl groups, cycloalkyl groups such as cyclohexyl group, alkenyl groups such as vinyl and allyl groups and aryl groups such as phenyl and tolyl groups as well as those substituted hydrocarbon groups obtained by replacing a part or all of the hydrogen atoms in the above named hydrocarbon groups with halogen atoms.

The group denoted by R in the general formula (I), which is bonded to the silicon atom in the silyl group substituting each of the phenyl groups at the 3- or 5-position, is a hydrogen atom or a monovalent hydrocarbon group exemplified by the same particular groups given above as the examples of the hydrocarbon group for $R^1$. When the intended application of the inventive fluorine-containing amide compound is as a crosslinking agent of a silicone rubber composition curable by the hydrosilation crosslinking reaction, it is preferable that each of the four silyl groups bonded to each of the benzene rings by twos is a dimethylsilyl group of the formula —SiMe$_2$H or a dimethyl vinyl silyl group of the formula —SiMe$_2$Vi, Me and Vi being a methyl group and a vinyl group, respectively. Namely, the compound having dimethylsilyl groups serves as a crosslinking agent for an organosilicon compound having at least two silicon-bonded vinyl groups in a molecule by effecting the hydrosilation reaction in the presence of a platinum catalyst while the compound having dimethyl vinyl silyl groups serves as a crosslinking agent for an organosilicon compound having at least two silicon-bonded hydrogen atoms in a molecule by effecting the hydrosilation reaction in the presence of a platinum catalyst.

Examples of the particularly preferable compounds which serve as a crosslinking agent of silicone rubber compositions therefore include, though not particularly limitative thereto, those expressed by the following structural formulas:

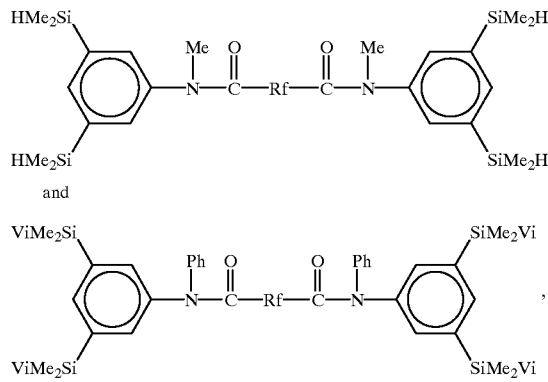

in which Rf, Me and Vi each have the same meaning as defined above and Ph is a phenyl group.

The fluorine-containing amide compound defined by the general formula (I) can be easily prepared according to the following synthetic procedure. Thus, a reaction mixture is prepared by admixing a perfluoroalkylene dicarboxylic acid difluoride represented by the general formula F—CO—Rf—CO—F, in which Rf has the same meaning as defined before, and an N-trimethylsilyl-N-(3,5-disilylphenyl) amine compound represented by the general formula

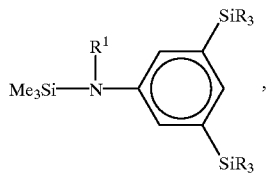

in which Me, R and R$^1$ each have the same meaning as defined before, with addition of a catalytic compound such as triethylamine, pyridine and the like and the reaction mixture is heated at a temperature in the range from 20 to 100° C. or, preferably, from 20 to 50° C. The reaction mixture is preferably diluted with a suitable organic solvent such as m-xylene hexafluoride. The above mentioned starting reactant compounds each can be synthesized according to the synthetic method shown below. Namely, the perfluoroalkylene dicarboxylic acid difluoride is prepared according to the procedure described in U.S. Pat. No. 3,660,315.

The N-trimethylsilyl-N-(3,5-disilylphenyl) amine compound or, typically, N-methyl-N-trimethylsilyl-N-[3,5-bis (dimethylsilyl)phenyl] amine can be synthesized according to the following synthetic route. Thus, 3,5-dichloroaniline is reacted with trimethyl monochlorosilane to give N-trimethylsilyl-N-(3,5-dichlorophenyl) amine and this compound is then methylated in a Grignard reaction with methyl chloride to give N-methyl-N-trimethylsilyl-N-(3,5-dichlorophenyl) amine which is finally converted in another Grignard reaction with dimethyl monochlorosilane into desired N-methyl-N-trimethylsilyl-N-[3,5-bis (dimethylsilyl)phenyl] amine.

The fluorine-containing amide compound of the present invention is a useful compound in a variety of applications. When the compound has two or, preferably, three or more of hydrogen atoms as R directly bonded to the silicon atoms in a molecule, for example, the compound serves as a crosslinking agent for an organosilicon compound or, in particular, an organopolysiloxane compound having two or more of vinyl or allyl groups bonded to the silicon atoms in a molecule in the presence of a catalytic compound such as a platinum compound having activity of promoting the hydrosilation reaction to give a cured elastomer. Alternatively, the compound of the invention having two or, preferably, three or more of vinyl groups bonded to the silicon atoms in a molecule serves as a crosslinking agent for an organosilicon compound or, in particular, organopolysiloxane having two or more of hydrogen atoms directly bonded to the silicon atoms in a molecule. As a consequence of the high fluorine content of the inventive compound, the cured elastomer obtained by such a crosslinking reaction has excellent resistance against solvents and chemicals and has a low surface energy to exhibit good surface releasability and water repellency so that the curable composition formulated with the inventive compound is useful as a sealant, molding composition by extrusion molding, coating composition, surface-release agent and the like.

Furthermore, absence of any siloxane linkages in the molecular structure of the inventive compound provides a possibility of obtaining a cured polymeric material free from siloxane linkages by the crosslinking reaction between the inventive compound having silicon-bonded hydrogen atoms and a non-siloxane polymeric compound having silicon-bonded vinyl or allyl groups or between the inventive compound having silicon-bonded vinyl or allyl groups and a non-siloxane polymeric compound having silicon-bonded hydrogen atoms while such a non-siloxane cured polymeric material is expected to exhibit much superior resistance against chemicals or, in particular, strong acids or strong alkalis as compared with polysiloxane-based cured polymeric materials of which the siloxane linkages have relatively high susceptibility to the attack of acids and alkalis.

In the following, an Example is given to illustrate the present invention in more detail although the scope of the present invention is never limited by the Example in any way.

EXAMPLE

A three-necked glass flask of 100 ml capacity equipped with a thermometer, Dimroth condenser and dropping funnel and containing a magnetic stirrer rotor was charged with 10.9 g (0.01 mole) of a perfluoroalkylene dicarboxylic acid difluoride expressed by the structural formula

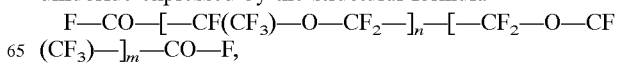

In which the subscripts m and n are each a positive integer with the proviso of m+n=6, 20.0 g of m-xylene hexafluoride and 0.6 g of triethylamine to form a mixture, into which 5.9 g (0.02 mole) of N-methyl-N-trimethylsilyl-N-[3,5-bis (dimethylsilyl)phenyl] amine were added dropwise through the dropping funnel under agitation with the magnetic stirrer and, after completion of the dropwise addition of the amine compound, the reaction mixture was heated at 50° C. for 2 hours to effect the coupling reaction between the difluoride compound and the anilide compound. After completion of the reaction, the reaction mixture was freed from the solvent by stripping at 120° C. under a reduced pressure of 3 mmHg to give 14.3 g of a clear yellow liquid having a viscosity of 152 centistokes at 25° C., specific gravity of 1.3092 at 25° C. and refractive index of 1.4254 at 25° C.

The FIGURE of the accompanying drawing is an infrared absorption spectrum of the thus obtained reaction product which shows absorption bands assignable to the C—F bonds at wave numbers of 1128, 1241 and 1305 cm$^{-1}$, an absorption band assignable to the C=O bonds at 1697 cm$^{-1}$ and an absorption band assignable to the Si—H bonds at 2125 cm$^{-1}$.

Further, the product compound was subjected to the determination of the silicon-bonded hydrogen atoms as functional groups and the molar functionality equivalent was calculated to obtain a value of 0.267 mole Si—H/100 g, which value supported the conclusion that this compound had a structure expressed by the structural formula of:

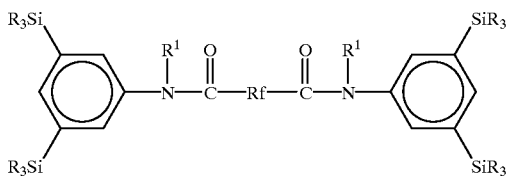

in which Me is a methyl group and the subscripts m and n are each a positive integer with the proviso that m+n=6. The above mentioned yield of the product compound corresponded to 95.6% of the theoretical value.

What is claimed is:

1. A compound represented by formula I

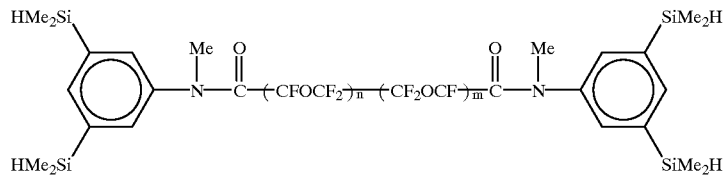

in which each R is, independently from the others, a hydrogen atom or a monovalent hydrocarbon group, each $R^1$ is, independently from the other, a hydrogen atom or a monovalent hydrocarbon group and Rf is a perfluoroalkylene group having 1 to 14 carbon atoms or a perfluoroalkylene group having at least 2 carbon atoms and interrupted by at least one oxygen atom between adjacent carbon atoms to form an ether linkage.

2. The compound of claim 1 in which R is selected from the group consisting of alkyl groups, cycloalkyl groups, alkenyl groups and aryl groups.

3. The compound of claim 1 in which $R^1$ is selected from the group consisting of alkyl groups, cycloalkyl groups, alkenyl groups and aryl groups.

4. The compound of claim 1 in which at least two of the silicon atoms in a molecule each have a hydrogen atom as R directly bonded thereto, the rest of the groups denoted by R each being a methyl group.

5. The compound of claim 1 in which at least two of the silicon atoms in a molecule each have a vinyl group or an allyl group as R directly bonded thereto, the rest of the groups denoted by R each being a methyl group.

6. The compound of claim 4 which is represented by formula II

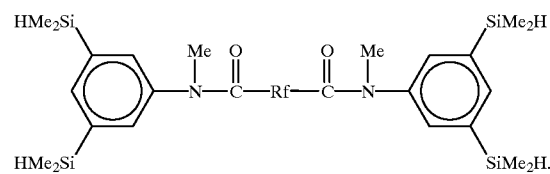

in which Me is a methyl group and Rf has the same meaning as defined in claim 1.

7. The compound of claim 5 which is represented by formula III

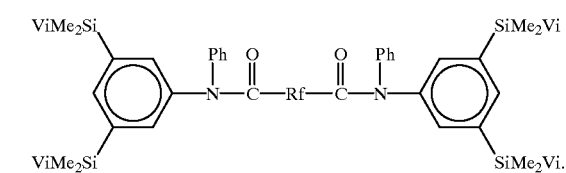

in which Ph is a phenyl group, Me is a methyl group and Rf has the same meaning as defined in claim 1.

8. A method for the preparation of a compound of claim 1 which comprises the steps of:

(a) mixing a perfluoroalkylene dicarboxylic acid difluoride represented by the formula F—CO—Rf—CO—F, in which Rf has the same meaning as defined in claim 1, and an N-trimethylsilyl-N-(3,5-disilylphenyl) amine compound represented by the formula IV

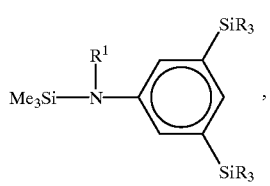

in which Me is a methyl group and R and $R^1$ each have the same meaning as defined in claim 1, to form a reaction mixture; and (b) heating the reaction mixture at a temperature in the range from 20 to 100° C.

9. The method of claim 8 in which the reaction mixture is admixed with a catalytic amount of triethylamine.

10. The method of claim 8 in which the reaction mixture is diluted with m-xylene hexafluoride.

11. The compound of claim 1 in which Rf is a perfluoroalkylene group havinf 4 to 8 carbon atoms.

12. The compound of claim 1 in which Rf is a perfluoropolyether represented by formula V

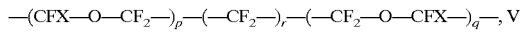

in which X is fluorine or trifluoromethyl, p and q are each, independently of the other, a positive integer with the proviso that p+q does not exceed 100, and r is 0 or a positive integer not exceeding 6, or by formula VI

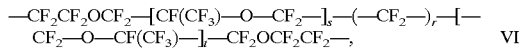

in which r is 0 or a positive integer nowt exceeding 6 and s and t are each, independently of the other, 0 or a positive integer with the proviso that s+t is a positibe integer in the range from 2 to 100, or by formula VII

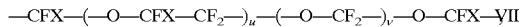

in which X is fluorie or trifluoromethyl, and u and v are each, independently of the other, a positive integer not exceeding 100, or by formula VII

in which w is a positive integer not exceeding 100.

13. The compound of claim 1 in which Rf is $-C_4F_8-$; $-C_6F_{12}-$; $-[CF(CF_3)-O-CF_2-]_n-[-CF_2-O-CF(CF_3)-]_m-$, wherein n+m is an integer in the range of 2 to 200; $-CF_2CF_2OCF_2CF(CF_3)-(-CF_2)_4-OCF(CF_3)CF_2O\ CF_2CF_2-$; $CF(CF_3)-[-OCF(CF_3)-CF_2-]_n-(-OCF_2-)_m-OCF(CF_3)-$, wherein n is an integer of 5 to 500 and m is a positive integer not exceeding 100; $-CF_2CF_2O-(-CF_2-)_4-OCF_2CF_2-$; $-CF_2-(-OCF_2CF_2-)_n-(-OCF_2-)_m-OCF_2-$, wherein n is an integer of 5 to 100 and m is a positive integer not exceeding 100; or $-CF_2CF_2-(OCF_2CF_2CF_2-)_n-OCF_2CF_2-$, wherein n is an integer of 5 to 100.

14. The compound of claim 3 in which $R^1$ is selected from the group consisting of methyl, ethyl, propyl, cyclohexyl, vinyl, allyl, phenyl and tolyl.

15. The compound of claim 2 in which R is selected from the group consisting of methyl, ethyl, propyl, cyclohexyl, vinyl, allyl, phenyl and tolyl.

16. The method of claim 8, in which said reaction mixture is heated at a temperature in the range from 20 to 50° C.

* * * * *